US006171813B1

(12) United States Patent
Dordick et al.

(10) Patent No.: US 6,171,813 B1
(45) Date of Patent: *Jan. 9, 2001

(54) ENZYME CATALYSIS IN ORGANIC SOLUTIONS CONTAINING WATER

(75) Inventors: Jonathan S. Dordick, Iowa City, IA (US); Vikram M. Paradkar, Madison, WI (US); Maria V. Sergeeva, Tiffin, IA (US)

(73) Assignees: BioTechnology Research & Develop. Corp., Peoria, IL (US); The University of Iowa Research Foundation, Iowa City, IA (US)

( * ) Notice: Under 35 U.S.C. 154(b), the term of this patent shall be extended for 0 days.

This patent is subject to a terminal disclaimer.

(21) Appl. No.: 08/951,506

(22) Filed: Oct. 16, 1997

Related U.S. Application Data

(63) Continuation of application No. PCT/US96/08726, filed on Jun. 3, 1996, which is a continuation-in-part of application No. 08/457,758, filed on Jun. 1, 1995, now Pat. No. 5,719,039.

(51) Int. Cl.$^7$ ............................... C12P 1/00; C12P 21/06; C12N 9/00; C12N 11/04
(52) U.S. Cl. ........................... 435/41; 435/68.1; 435/182; 435/183; 435/195; 435/213
(58) Field of Search ........................... 435/41, 68.1, 182, 435/183, 195, 213

(56) References Cited

U.S. PATENT DOCUMENTS

| 4,870,016 | 9/1989 | Levesque et al. | 435/183 |
| 5,316,935 | 5/1994 | Arnold et al. | 435/222 |
| 5,413,935 | 5/1995 | Patel et al. | 435/280 |

FOREIGN PATENT DOCUMENTS 3-280880  12/1991  (JP).

OTHER PUBLICATIONS

Biotechnol. Prog., (1992), vol. 8, pp. 259–267, "Designing Enzymes for Use in Organic Solvents", Jonathan S. Dordick.

Biotechnol. Bioeng., (1992), vol. 39, pp. 392–397 "Organic Solvents Strip Water Off Enzymes", Lu Ann S. Gorman et al.

Genetic Engineering News, Apr. 15, 1995, "Biocatalysis Technology in the 1990's Offers Novel Tools and New Choices", Cort Wrotnowski, pp. 10–11.

Journal of the American Chemical Society, Jun. 1, 1994, vol. 116, No. 11, pp. 5009–5010, "Aqueous–like Activity of α–Chymotrypsin Dissolved in Nearly Anhydrous Organic Solvents", Vikram M. Paradkar et al.

Biotechnol. Bioeng., (1994), vol. 43, pp. 529–540, "Mechanism of Extraction of Chymotrypsin into Isooctane at Very Low Concentrations of Aerosol OT in the Absence of Reversed Micelles", Vikram M. Paradkar et al.

The Journal of Biological Chemistry, Mar. 5, 1988, pp. 3194–3201, vol. 263, No. 7, "Enzymatic Catalysis in Nonaqueous Solvents", Aleksey Zaks et al.

Journal of the American Chemical Society, Dec. 29, 1993, vol. 115, No. 26, "Protein and Solvent Engineering of Subtilisin BPN' in Nearly Anhydrous Organic Media" Pramod P. Wangikar et al.

(List continued on next page.)

Primary Examiner—Jon P. Weber
(74) Attorney, Agent, or Firm—Venable; Michael A. Gollin

(57) ABSTRACT

A method is presented for catalyzing the conversion of substrate into product in an organic reaction solvent with an enzyme-surfactant ion pair. The enzyme-surfactant ion pair comprises the enzyme catalyzing the reaction and a surfactant capable of forming an ion pair with the enzyme. Water present in the organic solvent at a concentration of about 0.03% to about 2.5% is sufficient to enhance the rate of catalysis and stabilize the enzyme without substantially increasing the rate of hydrolysis when compared to the anhydrous enzyme.

20 Claims, 8 Drawing Sheets

OTHER PUBLICATIONS

Biocatalysis, (1990), vol. 3, pp. 227–233, "Enzymes in Organic Synthesis VII—Enzymatic Activity of HRP After Chemical Modification of the Carbohydrate Moiety", Didier Arseguel et al.

Journal of American Chemical Society, 1993, vol. 115, No. 4, pp. 1261–1264, "Structure and Stability of Insulin Dissolved in 1–Octanol", James Matsuura et al.

J. Chem. Soc. Chem. Commun., 1988, pp. 1392–1394 "A Lipid–coated Lipase as a New Catalyst for Triglyceride Synthesis in Organic Solvents", Yoshio Okahata et al.

Eur. J. Biochem., (1985), pp. 453–468, vol. 155, "Micellar Enzymology", Karel Martinek et al.

Biotechnol. Bioeng., (1992), vol. 40, pp. 91–102, "Mechanisms of Protein Solubilization in Reverse Micelles", S. F. Matzke et al.

Journal of the American Chemical Society, 1986, vol. 108, pp. 2767–2768, "Substrate Specificity of Enzymes in Organic Solvents vs. Water is Reversed", Aleksey Zaks et al.

Journal of the American Chemical Society, 1994, vol. 116, pp. 2647–2648, "Salts Dramatically Enhance Activity of Enzymes Suspended in Organic Solvents", Yuri L. Khmelnitsky et al.

Nature, Nov. 20, 1980, vol. 288, pp. 280–283, "A New Class of Angiotensin–converting Enzyme Inhibitors", A. A. Patchett et al.

Journal Chem. Soc. Faragls. Trans., (1986), vol. 82, pp. 1755–1770, "Interfacial Tension Minima in Oil–Water–Surfactant Systems", Robert Aveyard et al.

Biotechnology Progress, 1993, vol. 9, No. 2, pp. 199–203, "Affinity–Based Reverse Micellar Extraction and Separation (ARMES) : A Facile Technique for the Purification of Peroxidase from Soybean Hulls", Vikram M. Paradkar et al.

The Journal of Physical Chemistry, 1988, vol. 92, No. 12, pp. 3505–3511, "Cytochrome c in Sodium Bis(2–ethylhexyl) Sulfosuccinae Reverse Micelles: Structure and Reactivity", P. Brochette et al.

The Journal of Physical Chemistry, 1993, vol. 97, pp. 3631–3640, "Solubilization Mechanism of Cytochrome c in Sodium Bis(2–ethylhexyl) Sufosuccinate Water/Oil Microemulsion", Motonari Adachi et al.

Biotechnology Progress, Mar. 1985, vol. 1, No. 1, pp. 69–74, "Protein Extraction Using Reverse Micelles", Kent E. Göklen et al.

Biotechnology Progress, 1992, vol. 8, No. 1, pp. 85–90, "Release and Recovery of Porcine Pepsin and Bovine Chymosin from Reverse Micelles: A New Technique Based on Isopropyl Alcohol Addition", A. Carlson et al.

Biotechnol. Bioeng., (1991), vol. 38, pp. 1302–1307, "Selective Separation and Purification of Two Lipases from Chromobacterium viscosum Using AOT Reversed Micelles", M. R. Aires–Barros et al.

Carrea et al, (1995), *Trends Biotechnol,* 13, "Role of Solvents in the Control of Enzyme Selectivity in Organic Media", pp. 63–70.

Jones (1986) *Tetrahedron,* 42(13), "Enzymes in Organic Synthesis", pp. 3351–3403.

Bender et al. (1966) *J. Am. Chem. Soc.,* 88, "The Determination of the Concentration of Hydrolytic Enzyme Solutions: α–Chymotrypsin, Trypsin, Papain, Elastase, Subtilisin, and Acetylcholinesterase", pp. 5890–5913.

Tsuzuki et al. (1995) *J. Am. Oil Chem. Soc.,* 72(11), "Kinetics of Organic Solvent–Soluble and Native Lipase", pp. 1333–1337.

Bruno et al., "Enzymatic Modification of Insoluble Amylose in Organic Solvents", Marcomolecules, vol. 28, No. 25, pp. 8881–8883, (1995).

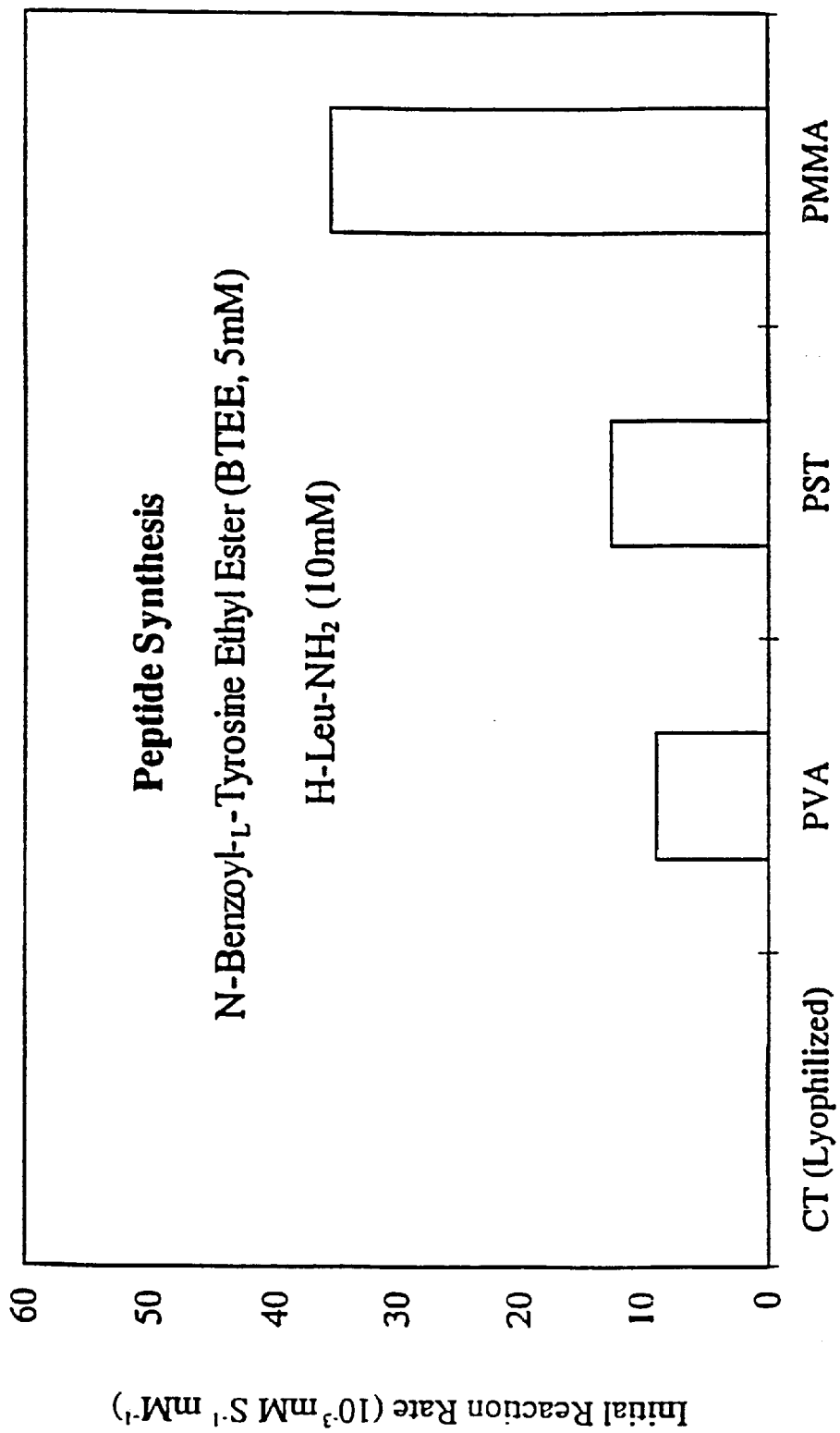
Fig. 7 Activity of α-Chymotrypsin-Containing Polymers in a Mixture of Isooctane/THF (70/30, v/v)

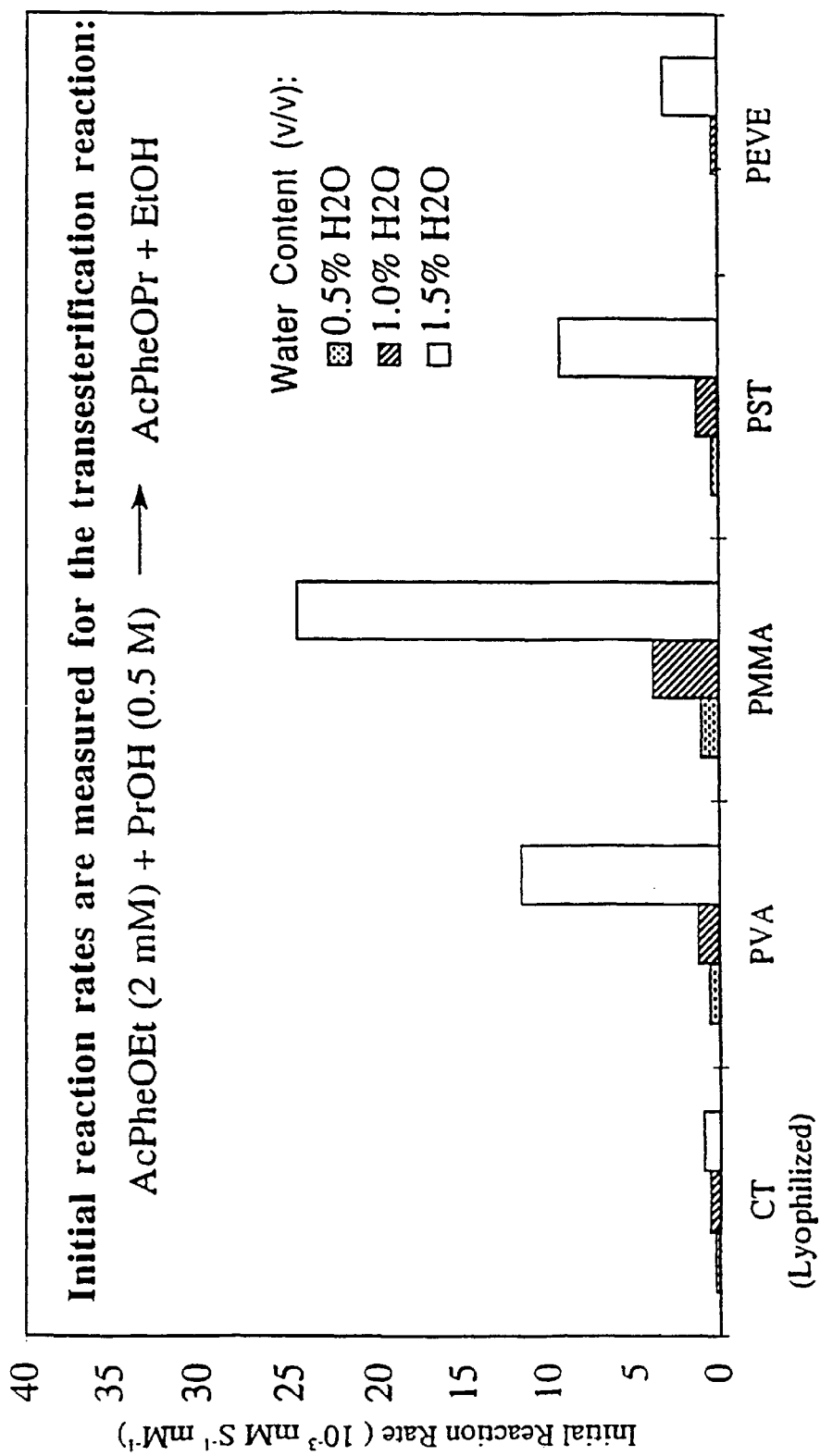
Fig. 8 Activity of α-Chymotrypsin-Containing Polymers in *tert*-Amyl Alcohol with Small Amounts of Water

ENZYME CATALYSIS IN ORGANIC SOLUTIONS CONTAINING WATER

This application is a continuation of PCT/US96/08726, filed Jun. 3, 1996, the U.S. being designated, which is a continuation-in-part of U.S. Ser. No. 08/457,758, filed Jun. 1, 1995, now allowed, the specifications of which are incorporated herein by reference.

BACKGROUND OF THE INVENTION

1. Field of the Invention

The present invention relates to enzyme-surfactant ion pairs with high catalytic activity and solubility in organic solution. More specifically, the invention relates to the solubilization of hydrolases in organic solvents without reversed micelles, and to enzyme-catalyzed reactions such as peptide synthesis with aqueous-like activity.

2. Related Art

The longstanding desire to achieve catalysis in organic liquids has led to several approaches. Chymotrypsin can be extracted from acidic aqueous solutions into organic solvents at very low surfactant concentrations (e.g., <2 mM) via ion-pairing of a surfactant with the protein. Paradkar and Dordick, *Biotechnol. Bioeng.* 1994, 43, 529 ("Paradkar & Dordick 1994"). It was shown in Paradkar & Dordick 1994 that an ion-paired complex of chymotrypsin and an anionic surfactant can be extracted into isooctane in the absence of reversed micelles. This led to the general suggestion that the CT-surfactant complexes may have direct application for preparing biocatalysts active and stable in homogeneous organic solutions.

SUMMARY OF THE INVENTION

It is an object of the invention to provide improved catalysis with stable catalytic enzyme-surfactant complexes that can be dissolved in an organic solvent, maintain their native structure, and exhibit high catalytic activities approaching those of aqueous solutions, and exceeding the activity of a catalyst obtained by optimizing extraction variables and the water content of the reaction medium.

It is another object of the invention to provide methods for enzyme catalysis in organic solutions containing water.

According to the invention, catalytic enzyme-surfactant ion pair complexes can be obtained by extraction from aqueous solution into organic solution, in substantially dehydrated form. These catalytic complexes can be obtained at maximal activity and can be used in a wide variety of catalytic reactions requiring homogeneous organic solutions. These complexes remain dissolved, maintain their native structure, and exhibit high catalytic activities which approach that in aqueous solutions.

An inventive method for improving catalysis by an enzyme-surfactant ion pair complex in an organic reaction solvent comprises providing greater than about 0.03% water in the organic reaction solvent, sufficient to extend the half life of the catalyst and to increase the catalytic efficiency of the catalyst.

A method of catalysis in an organic reaction solvent according to the invention comprises the steps of:

(a) obtaining a catalyst comprising a pre-activated enzyme-surfactant ion pair complex comprising an enzyme and an ionic surfactant capable of forming an ion pair complex with the enzyme, the complex having catalytic efficiency at least an order of magnitude greater than a suspension of an equal amount of the enzyme in the organic reaction solvent without surfactant, and produced by a process comprising dissolving the enzyme in an aqueous solution at a pH of maximal enzyme activity and agitating the enzyme-containing aqueous solution with an aqueous-immiscible organic extraction solvent and the dissolved ionic surfactant so as to extract the enzyme into the organic extraction solvent as a surfactant-enzyme ion pair complex, the ratio of surfactant to enzyme being less than that necessary to form reversed micelles, (b) combining the catalyst with an organic reaction solvent, comprising an organic solvent and water in an amount sufficient to maximize the rate of catalysis and stabilize the activated enzyme without substantially increasing hydrolysis, and ranging from about 0.03% to about 2.5% v/v, (c) adding to the organic reaction solvent at least one substrate for the enzyme, and (d) allowing a sufficient time for the enzyme to catalyze conversion of the substrate to a product.

The water content of the reaction solvent preferably does not exceed the water saturation point for the organic solvent containing the surfactant. The molar ratio of water to enzyme in the organic reaction solvent is preferably less than about 75:1.

The invention contemplates adding up to 2.5% v/v water to the reaction solvent, which may comprise a water miscible hydrophilic organic solvent. Preferably, the amount of water in the reaction solvent is between about 0.1% and about 0.3%, and the half life of the enzyme activity of the catalyst is at least about 0.25 hours, more preferably at least about one hour. The number of turnovers catalyzed by the enzyme-surfactant ion pair complex in the organic reaction solvent during one half life is preferably greater than that of the enzyme dissolved in water.

Preferably, the substrate is added to the organic reaction solvent continuously during conversion of the at least one substrate to a product, and the product is removed from the organic reaction solvent continuously during conversion of the at least one substrate to a product. Or the conversion is carried out as a batch process, in which the reaction is substantially completed before recovering the product, preferably by precipitating the enzyme from the organic reaction solvent by removal of the surfactant from the enzyme-surfactant complex after adding the substrate.

The substrate preferably comprises a blocked or unblocked acyl donor and a nucleophile, and may be an amino acid, an amino acid ester, an N-blocked amino acid, an N-blocked amino acid ester, an amino acid amide, an N-blocked amino acid amide, a polypeptide, a polypeptide ester, an N-blocked polypeptide, an N-blocked polypeptide ester, a polypeptide amide, an N-blocked polypeptide amide, an acyl donor is a methyl or ethyl ester of tyrosine, tryptophan, alanine, or phenylalanine, a methyl or ethyl ester of a dipeptide or tripeptide containing any of tyrosine, tryptophan, alanine, or phenylalanine, or an N-benzoyl, N-acetyl, or N-carbobenzoxy derivative thereof. The acyl donor and nucleophile are preferably added in a ratio between about 2:1 and 1:2.

The enzyme may be a catalytic antibody, an oxidoreductase, a transferase, a lyase, an isomerase, or a ligase, a hydrolase with acyl transferase activity in organic solvents, a peroxidase catalyzing phenolic polymerizations, a tyrosinase catalyzing aromatic hydroxylations, an alcohol dehydrogenase catalyzing stereoselective oxidation and reduction, a lipase, a nuclease, an aldolase, a phosphatase, a sulfatase, subtilisin, papain, pepsin, thermolysin, or thrombin.

The first step of the inventive method may involve (1) forming a two-phase aqueous/organic system comprising (i) a pre-activated enzyme solution produced by dissolving the enzyme in the aqueous solution at a pH of maximal enzyme activity, the aqueous solution having an enzyme concentration of from about 1 µg/ml to about 10 mg/ml, and ionic strength less than about 80 mM, (ii) an organic extraction solvent that is immiscible with water, and (iii) an ionic surfactant, the molar ratio of surfactant to enzyme in the two-phase system being sufficient to form an enzyme-surfactant ion pair complex, and substantially less than that necessary to form reversed micelles in the organic solvent;

(2) then agitating the two-phase system for a period sufficient to produce an ion pair complex of the pre-activated enzyme and the ionic surfactant and to extract the ion pair complex directly from the aqueous solution into solution in the organic extraction solvent, without substantial formation of reversed micelles;

(3) then separating the organic phase from the aqueous phase, whereby a homogeneous organic enzyme solution is obtained containing dissolved pre-activated enzyme-surfactant ion pair complex and essentially no reversed micelles.

The organic extraction solvent may be dried after extraction by evaporating the organic extraction solvent after extraction. In one embodiment, the enzyme is α-chymotrypsin, the surfactant is Aerosol OT, AOT, the pH of the aqueous activating solution is from about 7.0 to about 8.5, the ionic strength is less than about 20 mM, the enzyme:surfactant ratio is about 1:30 and the enzyme surfactant ion pair has a catalytic efficiency $k_{cat}/K_m$ in isooctane for the transesterification of N-acetyl-L-phenylalanine ethyl ester with 1-propanol of greater than 3000 $M^{-1}$ $s^{-1}$. In a preferred embodiment, the volumes of aqueous solution and organic extraction solvent are about equal, the starting concentration of surfactant in the organic solvent is about 2 mM, and the starting concentration of the enzyme in the aqueous solvent is about 1 mg/ml. If the surfactant is cationic, the pH of maximum activity is preferably above the pI of the enzyme.

Preferably, the ratio of surfactant to enzyme is less than about half of the reversed micelle ratio, more preferably between about one tenth and about one half of the reversed micelle ratio, less than about half of the reversed micelle ratio, less than about 80% of the stoichiometric amount necessary to fully cover the enzyme with surfactant, or less than about 90/110 of the reversed micelle ratio.

In another embodiment, the enzyme-surfactant ion pair complex is combined with a polymer to form a catalytic protein-polymer composite, and the protein-polymer composite is used as a catalyst in an organic solvent with beneficial amounts of water. Methods of doing so are disclosed in U.S. Provisional Patent Application Ser. No. 60/028,564, filed Oct. 10, 1996 (Dordick and Wang), which is incorporated herein by reference.

The polymer-protein composite can be used as catalyst particles, for example for use in packed-bed reactors. The packed bed reactors can be those used for peptide synthesis, glucose isomerization, selective penicillin hydrolysis, selective reactive separation of racemic mixtures of amino acids, drug, food, and beverage processing, and other processes. In such applications, catalysis may be continuous, with product removed with the supernatant, while the catalytic composite remains in the solid phase.

Further advantages, objectives, and embodiments are described below.

BRIEF DESCRIPTION OF THE DRAWINGS

The invention is illustrated by the following detailed description and figures.

FIG. 1 illustrates the effect of water content on the product yield, using 5.5 mM acyl donor, 10 mM nucleophile, and 3.6 µM soluble alpha-chymotrypsin.

FIG. 7 demonstrates the activity of immobilized α-chymotrypsin for peptide synthesis in a mixture of isooctane/THF. This represents the coupling of N-benzoyl-L-tyrosine ethyl ester (5 mM) with L-Leu-NH$_2$ (10 mM) to give the dipeptide in isooctane-THF (70:30, v/v) using α-chymotrypsin incorporated into different polymers. The PMMA (polymethylmethacrylate) composite shows an initial reaction rate of about 500 times higher than that of free enzyme suspension.

FIG. 8 demonstrates the activity of α-chymotrypsin incorporated into different polymers in the polar solvent tert-amyl alcohol (t-AA) with small amounts of water. This organic solvent is much more polar and hydrophilic than toluene or hexane. The free enzyme is poorly reactive in tert-amyl alcohol; however, the covalently incorporated enzyme in PMMA and PVA (polyvinylacetate), particularly, is reactive. Addition of water greatly stimulates the biocatalytic plastic, such that addition of 1.5%, v/v, water increases the activity over the dry suspended enzyme well over 26-fold. Water was added to the pure solvent (t-AA) prior to the addition of any substrates and enzyme/polymer composites.

DETAILED DESCRIPTION OF THE PREFERRED EMBODIMENTS

Figure 1A:
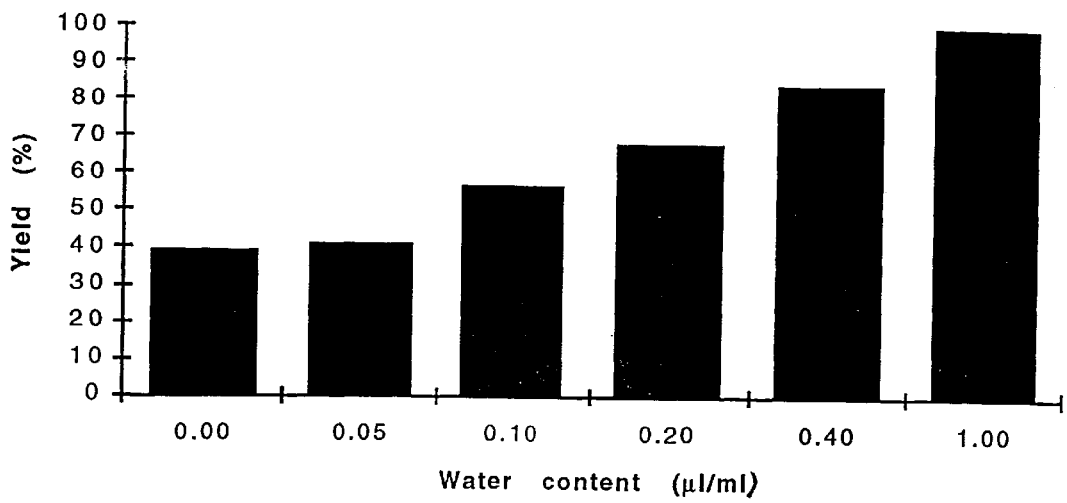
In FIG. 1A the acyl donor is Bz-Tyr-OEt (N-benzoyl tyrosine ethyl ester), the nucleophile is LeuNH$_2$ (leucine amide, in which the carboxyl group is blocked with an amino group to form an amide), and the product is Bz-Tyr-LeuNH$_2$ (N-benzoyl tyrosine leucine amide).

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Enzyme-surfactant ion pairs in organic solutions can be obtained according to the invention with catalytic activity approaching the levels in aqueous solution.

Preferably, the enzyme is dissolved in the aqueous solution, the surfactant is dissolved in the organic solvent (most surfactants are only slightly soluble in water) and the two phases are then combined. See Paradkar and Dordick, 1994, incorporated herein by reference.

EXAMPLE 1

Figure 1B:
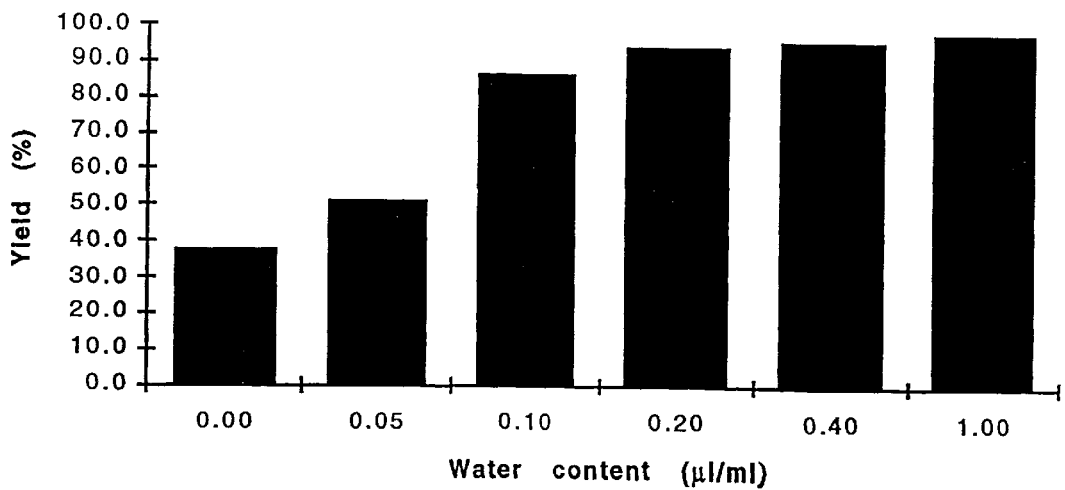
In FIG. 1B the acyl donor is the N-blocked dipeptide CBZ-Val-Tyr-OMe (N-carbobenzoxy-valine-tyrosine methyl ester), the nucleophile is LeuNH$_2$, and the product is the N-blocked tripeptide CBZ-Val-Tyr-LeuNH$_2$.

This example demonstrates the effect of added water on reactions catalyzed by chymotrypsin surfactant ion pairs. Two bar graphs for different reactions catalyzed by chymotrypsin are shown in FIG. 1A and FIG. 1B. The reactions are given above each graph and the effect of added water concentration (from 0 to 1 $\mu$l/ml) on each reaction yield is given. With N-benzoyl-L-tyrosine ethyl ester and 1-leucine amide, the maximal yield was obtained at 1 $\mu$l/ml. For N-carbobenzoxy-Val-Tyr methyl ester, maximal yields were obtained with water content as low as 0.2 $\mu$l/ml. It is clearly demonstrated that addition of very small concentrations of water (1 $\mu$l/ml=0.1%, v/v) is capable of increasing the reaction yield.

EXAMPLE 2

In this and the following examples, the goals were to find improved methods for enzyme solubilization in organic solvents through identification of the most advantageous surfactant/ion-paring agents; to provide improved structure, function, and dynamics of solubilized enzymes, particularly in hydrophilic (polar) organic solvents which are useful in peptide synthesis; and to provide methods for using solubilized proteases and lipases in the synthesis of peptides in organic solvents, particularly in dehydrated organic solutions.

Organic soluble enzymes exhibit extraordinarily high catalytic activities. α-chymotrypsin has catalytic efficiencies over 3-orders of magnitude higher in the solution state as compared to the suspended state in hydrophobic solvents such as octane or hexane for simple transesterification reactions. Surprisingly, this activation is also observed for peptide synthesis according to the invention.

Materials

α-chymotrypsin from bovine pancreas and subtilisin Carlsberg from *Baccillus lichenifonnis* were purchases from Sigma (St. Louis, Mo.). Aerosol OT (AOT, sodium bis(2-ethylhexyl)sulfosuccinate, >99% purity) was also obtained from Sigma and was used without further purification. Organic solvents were purchased from Aldrich (Milwaukee, Wis.) and were of the highest purity available. Solvents were stored over molecular sieves (Type 4 Å) for at least 24 hours prior to use. N-CBZ-L-Ala-L-Phe-OMe, N-CBZ-L-Ala-L-Ala-OMe, N-CBZ-L-Val-L-Trp-OMe, and L-Leu-NH$_2$ were from Bachem Bioscience Inc. (Switzerland). All other amino acid substrates were from Sigma Chem. Co. All reagents used in this work were of the highest grade commercially available.

Extraction Procedure

Extractions were performed on 1 mg of an enzyme in 1 ml of 10 mM Bis-Tris propane buffer solution, pH 7.8, containing 2 mM CaCl$_2$ and 1%, v/v, isopropanol. This solution was contacted with 1 ml of isooctane, containing 2 mM AOT. The biphasic mixture was stirred in ca. 250 rpm for 2 min. then the phases were allowed to settle for an additional 2 min. Clear phase separation was subsequently achieved by centrifuging at 6000 rpm for 1 min. The enzyme concentrations in the organic phase were calculated from the extinction coefficients of the enzymes in water. The organic phase was evaporated to dryness by bubbling N$_2$ through the isooctane solution. The residue of the soluble enzyme was re-dissolved in the solvent of choice and used for peptide synthesis. The amount of water in the solubilized enzyme preparations was determined by Karl Fisher titration.

The organic solution containing the biocatalyst can be dried in vacuo, and the ion-pared enzyme powder can be redissolved in a solvent of choice resulting in a transparent molecular solution of the enzyme in a nearly anhydrous organic solvent.

Peptide synthesis

The standard reaction mixture consisted of an N-protected amino acid ester as acyl donor, an amino acid amide as acyl acceptor, and the solubilized enzyme in 1 ml total volume. The concentrations of the ester and the amide were varied to obtain values of $k_{cat}/K_m$. In some cases small concentrations of water were added to the reaction mixture, but in no case did a biphasic system form. The reactions were performed at 3° C. under continuous agitation (250 rpm). Periodically, 200 $\mu$l aliquots were removed and the reactions terminated by addition of 20 $\mu$l glacial acetic acid. The samples were then evaporated to dryness under reduced pressure, the reaction products were dissolved in acetonitrile and quantitatively analyzed by HPLC (Shimadzu LC-10AS, fitted with a YMC-Pack ODS-AQ column and detected by absorbance at 280 nm). Elution was carried out isocratically with 40%, v/v, acetonitrile in aqueous solution containing 0.01%, v/v, trifluoroacetic acid (pH3).

Results

Organic solvent soluble α-chymotrypsin (CT) efficiently catalyzed the synthesis of a variety of dipeptides in isooctane containing 30% (v/v) tetrahydrofuran (THF); the polar solvent was added to aid in substrate solubility. The reaction of N-Bz-L-Tyr-OEt with L-Leu-NH$_2$ is suitable for both CT and subtilisin Carlsberg (SC) catalysis in a variety of organic solvents. The values of $k_{cat}/K_m$ for the organic soluble enzymes in isooctane (containing 30%, v/v, THF) was calculated to be 39 and 43 $M^{-1}s^{-1}$ for CT and SC, respectively. These values were dramatically higher than those for suspended CT and SC (0.04 and 0.02 $M^{-1}s^{-1}$, respectively. The activation by the solubilized enzymes is genuine; no reaction was observed in the absence of enzyme or in the presence of heat-inactivated enzyme (by boiling in water for 30 min prior to extraction into isooctane).

Thus, the soluble enzymes are sufficiently activated over their suspended counterparts for peptide synthesis. These findings demonstrate that enzymes in organic solvents can function with the same activity and selectivity as found in aqueous solutions, albeit with improved potential for commercially relevant syntheses.

Figure 2A:
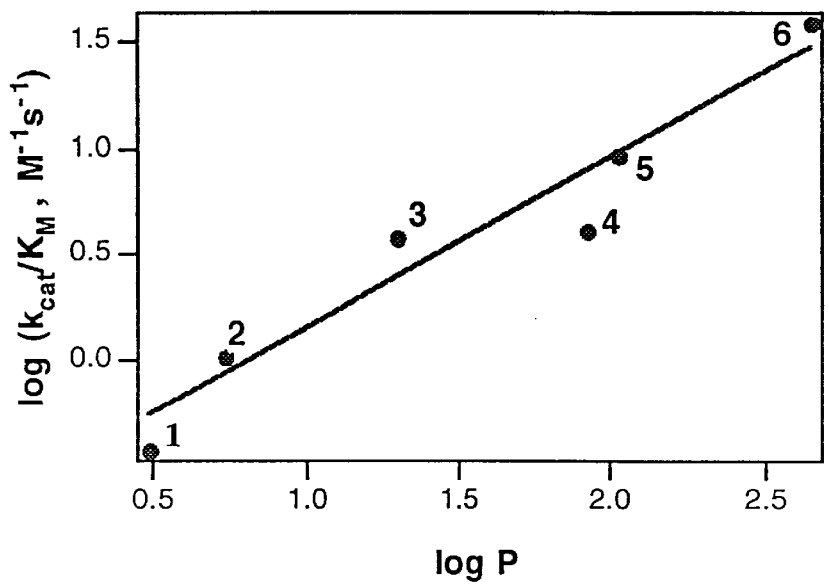
FIG. 2A graphs data for α-chymotrypsin.
Figure 2B:
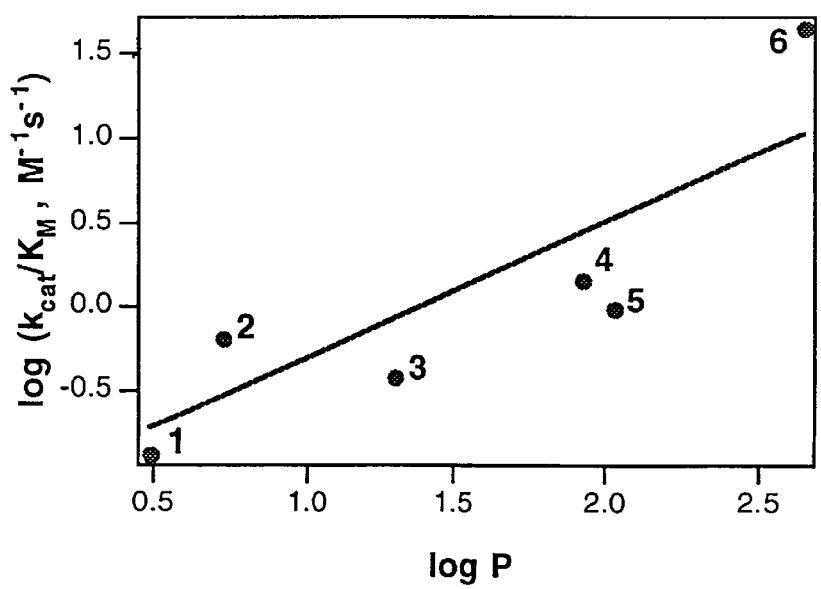
FIG. 2B shows results for subtilisin Carlsberg. The acyl donor was N-Bz-L-Tyr-OEt, and the acyl acceptor was L-Leu-N$_2$. Solvents: 1—THF, 2—ethyl acetate, 3—methylene chloride, 4—butyl acetate, 5—isopropyl ether, 6—isooctane (containing 30%, v/v THF).

The activity of both enzymes is strongly affected by the hydrophobicity of the organic solvent. As depicted in FIGS. 2A and 2B, both organic soluble CT and SC were strongly activated in hydrophobic organic solutions. Indeed, the values of $k_{cat}/K_m$ are increased over 100-fold for CT and over 300-fold for SC in going from neat THF to isooctane (containing 30%, v/v, THF). This striking solvent effect is more pronounced for organic solvent soluble enzymes than for their suspended counterparts for similar reactions. For example, the $k_{cat}/K_m$ of the related subtilisin BPN'-catalyzed transesterification of N-Ac-L-Phe-OEt with n-PrOH is not substantially different in a hydrophobic solvent such as hexane and a hydrophilic solvent such as acetone. Without intending to be limited to this theory, it can be surmised that the suspended enzyme particles act as a buffer between the inactivating effects of hydrophilic organic solvents and the individual enzyme molecules. Soluble enzymes do not have such a protective mechanism.

EXAMPLE 3

Enzymatic peptide synthesis using soluble enzymes in organic solvents is dramatically improved upon addition of small concentrations of water. This enables reactions to be performed in ethyl acetate, which was selected as a representative hydrophilic solvent that can aid in dissolving peptidic substrates. The results are summarized in FIGS. 3A and 3B.

Figure 3A:
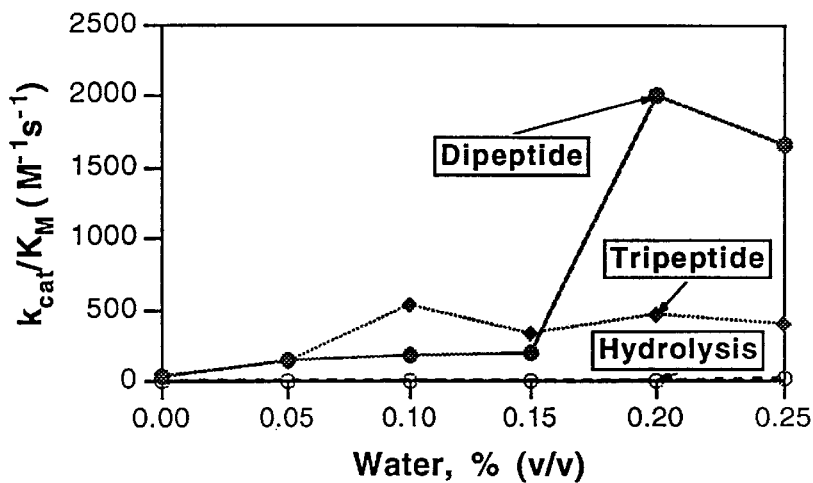
FIG. 3A—isooctane (containing 30%, v/v THF), and FIG. 3B—ethyl acetate.
Figure 3B:
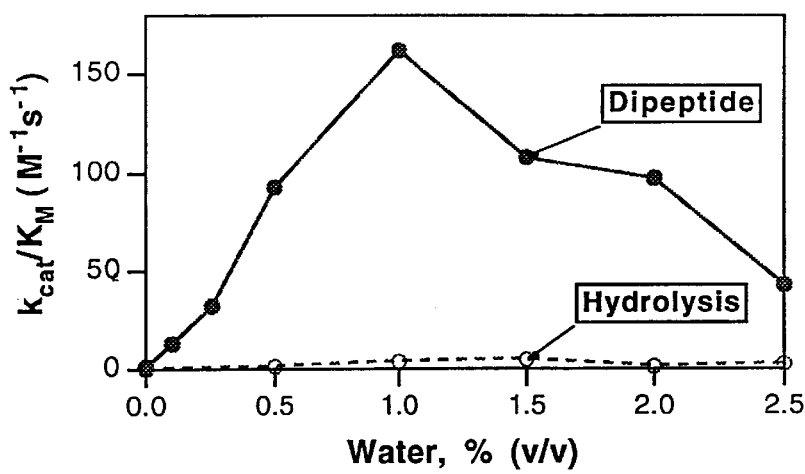
FIG. 3 shows the effect of added water on peptide synthesis catalyzed by soluble α-chymotrypsin. The acyl donors were N-Bz-L-Tyr-OEt or N-CBZ-L-Val-L-Tyr-OMe, and the acyl acceptor: L-LeuNH$_2$. Solvents.

Water activates CT catalysis in di- and tripeptide synthesis, the latter with CBZ-L-Val-L-Tyr-OMe as ester donor. In isooctane-THF solution, the addition of as little as 0.05%, v/v, water increased the value of $k_{cat}/K_m$ 3.5-fold, and this value was increased over 50-fold upon addition of 0.20%, v/v, water (FIG. 3A). Although the activation is not as significant for tripeptide synthesis with CBZ-L-Val-L-Tyr-OMe as the acyl donor, a 12-fold increase in $k_{cat}/K_m$ was obtained upon addition of 0.20%, v/v, water. The effect of added water is even more pronounced in ethyl acetate for dipeptide synthesis (FIG. 3B); the addition of 1.0%, v/v, water resulted in greater than a 150-fold activation when compared to the dry ethyl acetate solution. In both isooctane-THF and ethyl acetate, the activation by water did not lead to substantial hydrolysis of the ester donors. For example, even in the presence of 1.0%, v/v, water in ethyl acetate, the $k_{cat}/K_m$ for N-Bz-L-Tyr-OEt hydrolysis was nearly 50-fold lower than that for peptide synthesis. Thus, the reaction selectivity toward peptide synthesis remains high even in the presence of small concentrations of water.

The reason for the observed drop in $k_{cat}/K_M$ above 0.2% and 1.0%, v/v, water in isooctane-THF and ethyl acetate, respectively, is unclear. It is not due to a competing hydrolysis reaction as no increase in the rate of formation of N-Ac-L-Phe is observed. Instead, it is possible that a structural change in the enzyme occurs thereby resulting in a less reactive enzyme. Enzymes become more flexible as the hydration of the solvent increases, but increased flexibility does not always lead to increased activity. A case in point is the hydration of SC in THF: addition of <0.5%, v/v, water strongly activates SC; however, above this hydration level, the activity of SC drops precipitously. Thus, the degree of solvent (and hence enzyme) hydration can result in a complex behavior that is characterized by enhanced and diminished reactivity depending on the level of enzyme hydration. Such behavior is observed for CT catalysis in both isooctane-THF and ethyl acetate.

Of great advantage is the dramatic rate enhancement obtained in ethyl acetate in going from dry to 0.5% (v/v) added $H_2O$ for the synthesis of Bz-Tyr-Leu-$NH_2$ by CT. The addition of water also has minimal effect on reaction selectivity toward peptide synthesis. In both isooctane:THF (7:3) (FIG. 3A), and ethyl acetate (FIG. 3B), the addition of water (up to 0.25% (v/v) in isooctane and 0.5% or 1% (v/v) in ethyl acetate) had a minimal impact in the loss of ester substrate to hydrolysis. Thus, the selectivity of the reaction (toward peptide synthesis) is high. This finding has direct industrial application as it enables use of a solvent that is ideal for peptide synthesis reactions.

Figure 4A:
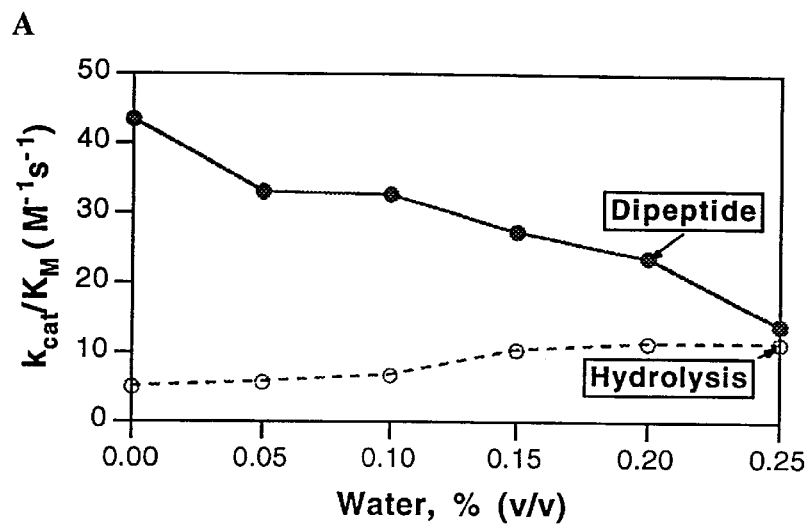
FIG. 4A—isooctane (containing 30%, v/v THF), and FIG. 4B—ethyl acetate.
Figure 4B:
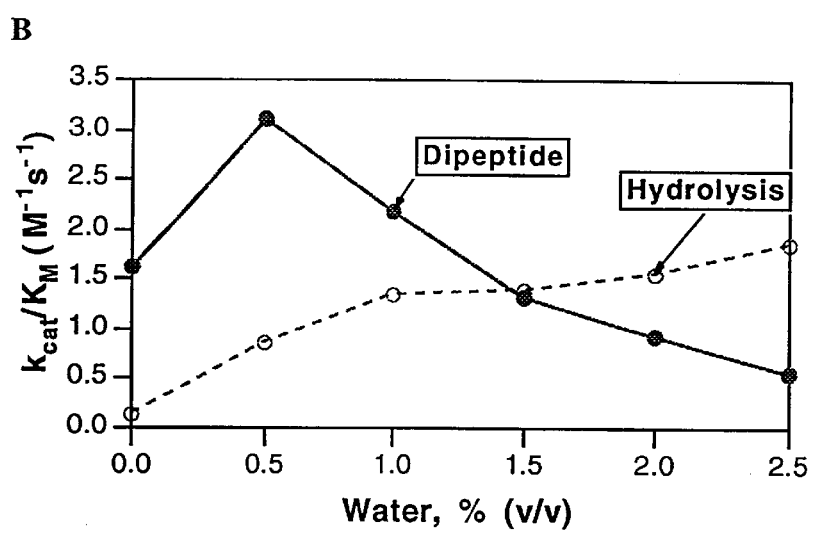
FIG. 4 demonstrates the effect of added water on peptide synthesis catalyzed by soluble subtilisin Carlsberg. The acyl donor was N-Bz-L-Tyr-OEt, and the acyl acceptor was L-Leu-NH$_2$. Solvents.

Unlike CT, the activation of SC upon partial hydration of isooctane-THF or ethyl acetate was not significant (FIGS. 4A and 4B), and actually resulted in substantial hydrolysis. Specifically, in isooctane-THF containing 0.25%, v/v, water, the $k_{cat}/K_m$ for hydrolysis is nearly as high as for peptide synthesis. Even in dry isooctane-THF, there was a significant fraction (>10%) of hydrolysis as compared to CT. Measurements of the water content on CT and SC in dry isooctane-THF indicated that both proteins have bound water contents of 7.5%, w/w.

The higher hydrolytic activity of SC relative to CT relates to the proclivity of SC for hydrolysis. SC, due to its more hydrophilic binding pocket, may have greater propensity for water as the nucleophile than for L-Leu-$NH_2$ as compared with CT. Hence, hydrolysis is a favorable reaction even in the presence of small concentrations of water. The small amount of water bound to the enzyme in the absence of added water is sufficient to promote some background hydrolysis.

Thus, according to the invention, the water present in the reaction solution is sufficient to stabilize the enzyme structure so as to maximize the rate of peptide synthesis but not so high as to cause substantially increased hydrolysis. A substantial increase in this context means about double the amount in dry organic solvent or about 50% of synthesis if there was no measurable hydrolysis in dry solvent. The amount of water added to dry organic solvent to provide a reaction solvent thus may be between about 0.025% to about 2.5%, preferably from about 0.05% to about 0.5%. With an enzyme having a hydrophobic active site such as CT, the preferred range is about 0.05% to about 0.15%, and in isooctane with 30% THF, v/v, the preferred amount is about 0.1%. In polar solvents such as ethyl acetate, the range is higher, preferably 0.5% to 2.0%, most preferably about 1.0%. For an enzyme with a hydrophilic active site such as subtilisin Carlsberg in isooctane, the minimum amount of added water is preferred. In a polar solvent, such as ethyl acetate, the range may be from about 0.25% to about 1.0%, preferably about 0.5%.

The amount of water added should further be sufficient to provide increased yield of the peptide reaction product as compared to dry reaction conditions. As shown in FIGS. 1A and 1B, the amount of water added to increase yield of a dipeptide and a tripeptide catalyzed by CT in isooctane/THF (70/30) was as low as 0.1%, preferably between about 0.05% and 0.1%. In general measurable increases in yield (e.g. 20%–100% increases) can be expected between about 0.01% and 0.2%.

EXAMPLE 4

CT-catalyzed peptide synthesis shows substrate specificity. CT is specific for bulky hydrophobic amino acids. The specificity of CT was examined in isooctane-THF and ethyl acetate solutions under optimal solvent hydration levels of 0.2 and 1.0%, v/v, added water, respectively. Values of $k_{cat}/K_m$ for the ester donor are depicted in Table I for two series of CBZ-dipeptide methyl esters, each of them differing in the $P_1$ amino acid residue. Table I shows values of $k_{cat}/K_m$ ($M^{-1}s^{-1}$) for organic solvent-soluble α-chymotrypsin-catalyzed peptide synthesis between different dipeptide esters and L-LeuNH$_2$. The amide concentration was fixed at 10 mM and the ester concentrations were varied from 1 to 10 mM. The enzyme concentration was 100 μg/ml. All experiments were performed in triplicate and standard errors determined to be <15% of the values presented in the table.

TABLE I

| Ester | Isooctane-THF 70:30 +0.2%, v/v water | Ethyl acetate +1%, v/v water |
|---|---|---|
| N—CBZ—L—Ala—L—Phe—OMe | 141 | 33.9 |
| N—CBZ—L—Ala—L—Val—OMe | 0.017 | 0.001 |
| N—CBZ—L—Ala—L—Ala—OMe | 3.75 | 0.53 |
| N—CBZ—L—Ala—Gly—OMe | 1.10 | 0.22 |
| N—CBZ—L—Val—L—Tyr—OMe | 455 | 33.2 |
| N—CBZ—L—Val—L—Trp—OMe | 75.6 | 14.3 |
| N—CBZ—L—Val—L—Phe—OMe | 71.9 | 10.4 |
| N—CBZ—L—Val—L—Leu—OMe | 6.59 | 0.71 |
| N—CBZ—L—Val—L—Ala—OMe | 2.21 | 0.52 |

The aromatic-containing dipeptides were highly reactive in both partially hydrated isooctane-THF and ethyl acetate. Thus, the soluble CT of the invention has hydrolytic specificity with a preference for hydrophobic amino acid residues comparable to CT in aqueous solutions and to CT-catalyzed peptide synthesis in organic solvents using suspended enzyme.

A direct comparison of the substrate specificity of the organic solvent soluble CT to the suspended enzyme was made using two of the CBZ-ipeptides in Table I; namely those with a Phe and an Ala in the $P_1$ position. Again using partially hydrated solvents, the values of $k_{cat}/K_m$ for the soluble enzyme were substantially higher (up to three orders of magnitude) than those of the suspended enzyme in isooctane-THF and ethyl acetate, respectively (Table II).

TABLE II

| | $k_{cat}/K_M$ ($M^{-1}s^{-1}$) | |
|---|---|---|
| Substrates | Isooctane-THF +0.2%, v/v water | Ethyl acetate +1%, v/v water |
| α-Chymotrypsin (suspended) | | |
| N—CBZ—L—Ala—L—Phe—OMe | 0.44 | 0.037 |
| N—CBZ—L—Ala—L—Ala—OMe | 0.2 | 0.01 1 |
| Ratio | 2.2 | 3.3 |
| α-Chymotrypsin (solubilized) | | |
| N—CBZ—L—Ala—L—Phe—OMe | 141 | 33.9 |
| N—CBZ—L—Ala—L—Ala—OMe | 3.75 | 0.53 |
| Ratio | 37.5 | 64 |

Moreover, the specificity ratio between the Phe- and Ala-containing dipeptides was markedly different between the two enzyme forms and between the two organic solvents. Specifically, the ratios of $(k_{cat}/K_m)_{Phe}(k_{cat}/K_m)_{Ala}$ for the suspended enzyme in isooctane-THF and ethyl acetate are a modest 2.2 and 3.3 respectively. These ratios are substantially increased with is the soluble CT to 37.5 and 64.03 in isooctane-THF and ethyl acetate, respectively. The ion-pared, organic soluble CT is more flexible than its insoluble counterpart. This flexibility provides a binding site that is more native-like (as in water) and capable of eliciting more native-like substrate specificities than the more rigid suspended enzyme form.

EXAMPLE 5

A variety of proteases and nonproteases are active in the solubilized state in organic solvents. Six different proteases were solubilized in isooctane (containing 1% isopropanol) in yields ranging from 23 to 70% (0.23 to 0.47 mg/ml), including α-chymotrypsin, subtilisin Carlsberg, subtilisin BPN', trypsin, thermolysin, and papain. Also glucose oxidase and soybean peroxidase can be solubilized for other applications including biosensors and bioremediation catalysts, respectively. The solubilization conditions were selected according to the methods of the invention, which provide for solubilizing all these proteins as surfactant ion pairs in organic solvents.

EXAMPLE 6

The stability and activity of subtilisin BPN' is increased in polar organic solvents upon the addition of very small concentrations of water. While the stability of soluble subtilisin BPN' is high in nonpolar solvent such as octane (Table III), substantial deactivation is observed in polar solvents such as tetrahydrofuran (THF). However, activation of the enzyme in THF is feasible upon addition of small concentrations of water. For example, addition of 0.2% (v/v) water increases the half-life at room temperature from 10 min (in dry solvent) to >40 min. Water has been shown to stabilize both the secondary and tertiary structure of the enzyme in THF. These studies have been extended to tert-amyl alcohol with similar stability enhancements.

Thus, the amount of water added to the reaction solvent according to the invention should be sufficient to provide enhanced stability, such as in the range of about 0.1% to about 0.3%, preferably about 0.2% for polar solvents and subtilisin. Enhanced stability means, in this context, at least a doubling of half life.

TABLE III

Kinetic Constants for Soluble Subtilisin BPN' in Various Solvents

| Solvent | $k_{cat}K_m(M^{-1}s^{-1})^a$ | Observed half-life (h)$^b$ |
|---|---|---|
| Octane | 370 ± 40 | 1400$^d$ |
| Aqueous buffer | 3500 ± 200$^c$ | 2.17 |
| Tetrahydrofuran | 0.04 ± 0.01 | 0.17 |
| THF + 0.2% H$_2$O | 0.36 ± 0.06 | 0.67 |
| tert-Amyl alcohol | 1.2 ± 0.2 | 1.67 |
| tert-Amyl alcohol + 0.2% H$_2$O | 2.8 ± 0.4 | n.d. |
| Octane (suspended) | 0.6 ± 0.1 | n.d. |

$^a$Catalytic constants determined for tranesterification between N—Ac—L—Phe—OEt (0.1–250 mM) and 1-P$_1$OH(0.5M) using 14–150 μg/ml subtilisin BPN'.
$^b$Observed half-life measured by incubating soluble subtilisin in the given solvent and then assaying the activity in aqueous buffer by transferring small aliquots of subtilisin solution to water.
$^c$Catalytic efficiency determined for hydrolysis of N—Ac—L—Phe—OEt (0.1–1.0 nM) in water using 10–50 μg/ml enzyme.
$^d$Observed half-life reported in oxane is an estimated value as the enzyme lost only 35% activity in 2 months when incubated in dry octane.

Soluble Enzyme Activity and Stability. The $k_{cat}/K_m$ of subtilisin BPN' dissolved in octane is nearly three orders of magnitude greater than that of the suspended enzyme in the same solvent (Table III). This exceptional activation of the enzyme results in a value of $k_{cat}/K_m$ in octane that is within one order of magnitude of the value in aqueous buffer, and demonstrates that the organic soluble enzyme is highly active in nonpolar, homogeneous organic solutions. Moreover, the enzyme is three orders on magnitude more stable to irreversible inactivation in octane than in aqueous buffer, presumably because of the absence of autolysis in the organic solvent. Therefore, over its active lifetime the productivity of the soluble enzyme is higher in octane than in water.

The benefits of solubilization are not observed in all organic solvents. For instance, values of $k_{cat}/K_m$ are dramatically lower in the more polar tert-amyl alcohol and tetrahydrofuran (THF) solutions (Table III). Indeed, the four orders of magnitude difference of $k_{cat}/K_m$ values between octane and THF correspond to a 7.7 kcal/mol destabilization of the transition state of subtilisin in THF as compared to octane. Whereas the measurable activity of soluble subtilisin is retained after several months storage in octane, activity in THF is lost in minutes. Furthermore, incubation in THF induces severe irreversible inactivation of soluble subtilisin. Specifically, only 50% of the activity can be recovered if soluble subtilisin is incubated in THF for 10 min and then transferred to water. As a practical matter, enzyme stability according to the invention should be greater than that of CT in dry THF, preferably at least about 0.25 hours, more preferably more than about 0.5 hours, and most preferably over an hour. A half life of over 10, 100, or 1000 hours is achievable according to the invention.

Effect of solvent hydration on enzyme activity. Compensating for possible stripping of water from the enzyme, causing lower catalytic efficiencies, additions of small concentrations (0.2%) of water in both THF and tert-amyl alcohol results in an increase in enzymatic activity of soluble subtilisin (Table III). The activity increases were almost ten fold and more than double respectively, which are significant increases. Coincidentally, the addition of 0.2% water to THF also improves the stability of soluble subtilisin by ca. 4-fold. Thus, addition of water to polar solvents improves activity and stability of soluble subtilisin.

EXAMPLE 7

Figure 5:
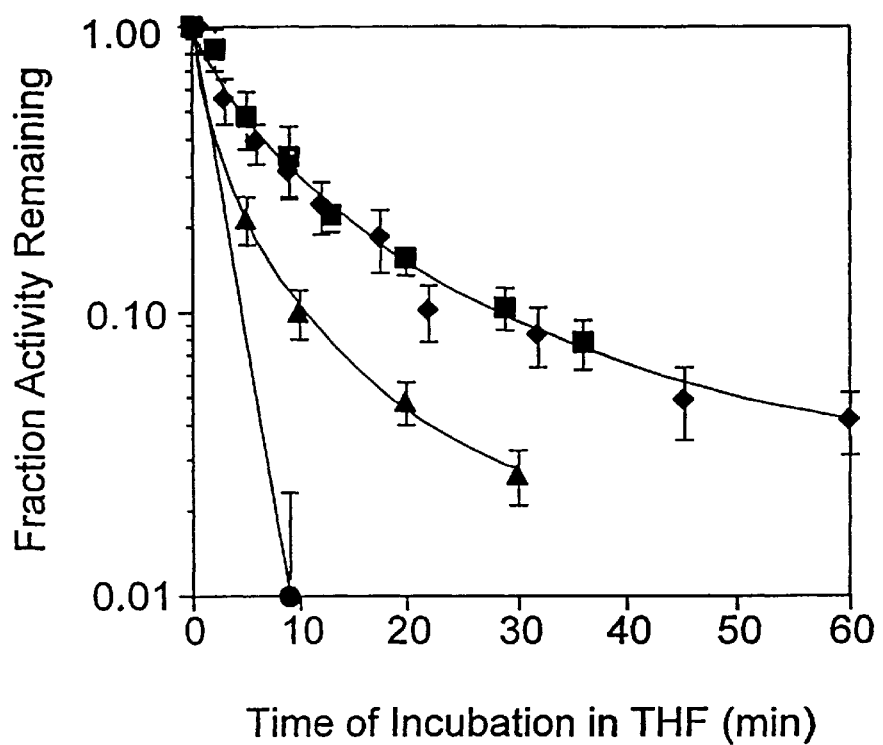
FIG. 5 depicts inactivation kinetics of subtilisin BPN' solubilized in dry THF. Soluble enzyme was incubated in THF for indicated periods of time and activity was measured in dry THF (circles), octane (triangles), and aqueous buffer (squares). Also, subtilisin was incubated in THF for different lengths of time, then transferred to octane, extracted into water after a 30 min further incubation in octane, and the activity assayed in water (diamonds). For the enzyme transferred from THF to octane, no further change in activity was observed for 24 hours in octane. The enzymatic activities are assayed for transesterification reaction between N-Ac-PheOet and 1-propanol in organic solvents, and for hydrolysis of suc-Ala-Ala-Pro-Phe-p-nitroanilide in water.
Figure 6:
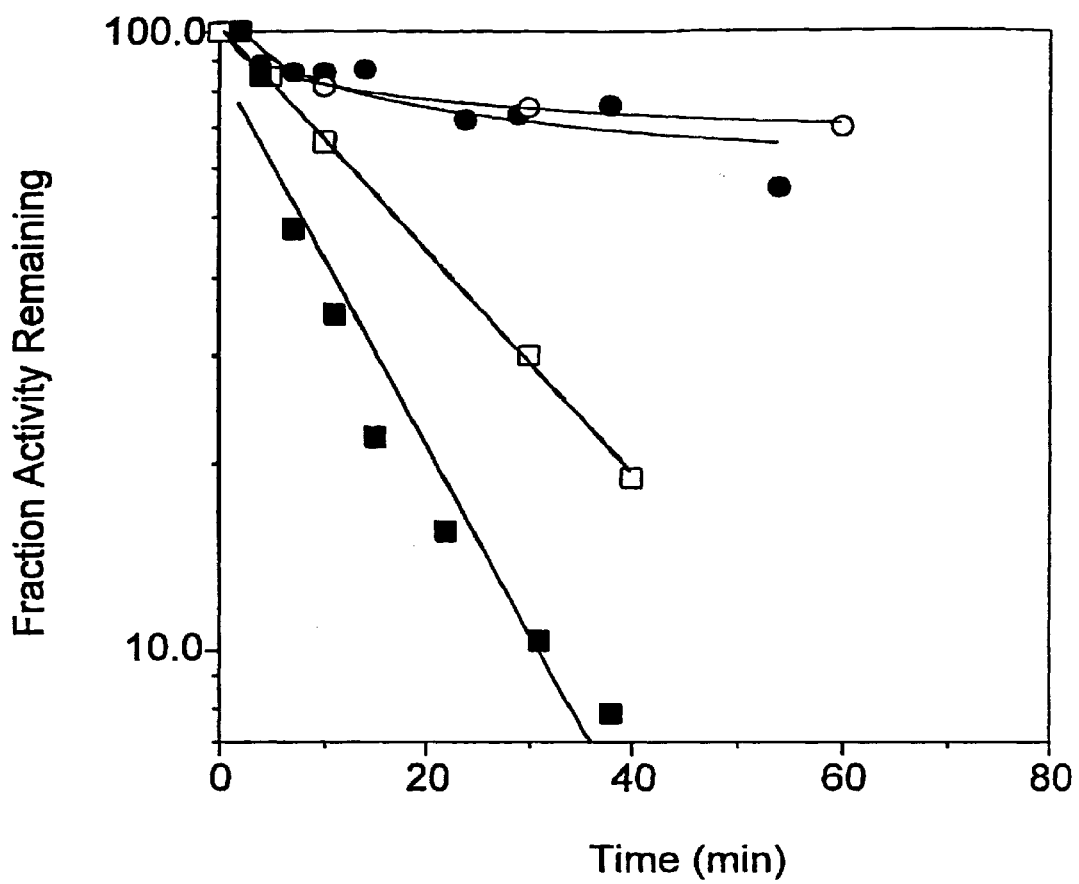
FIG. 6 shows relative stability of soluble subtilisin in dry THF (squares) and THF containing 0.2% added water (circles). Kinetics of irreversible inactivation were followed by incubating soluble subtilisin in THF (dry or containing 0.2% water) and transferring aliquots to water, measuring activity (filled symbols) and recording near-UV CD spectra (empty symbols) in water. The fraction of the native-like enzyme was estimated from the area under the near-UV CD spectrum.

Subtilisin BPN' can be refolded in octane. It is known that enzymes can be partially denatured in water and still be refolded to the native conformation. This has been extended to nonaqueous systems (FIG. 5). Specifically, subtilisin BPN' is denatured (loses its tertiary structure) in THF for short times (i.e., before secondary structure is lost), and then the enzyme is transferred to water. Refolding occurs and the enzyme regains its activity. Similarly, the denatured enzyme in THF is transferred to octane. As in water, the native enzyme structure is obtained and the activity is restored. This demonstrates that water is not required to fold protein-surfactant ion pairs according to the invention.

FIG. 5 depicts the fraction of native enzyme as a function of incubation time in both dry THF and THF supplemented with 0.2% (v/v) water. The rapid loss of catalytic activity in dry THF is concomitant with the loss of native tertiary structure of the enzyme. Hence, the loss of native tertiary structure appears to correlate with the loss in catalytic activity of THF, supporting the view that THF inactivates soluble subtilisin by disrupting the native teritary structure. Furthermore, the addition of a small concentration of water is sufficient to stabilize the tertiary structure of subtilisin, accompanied by an enhancement of the stability of the enzyme (Table III). Water appears to stabilize subtilisin in THF by helping to maintain its native structure.

Reversible and Irreversible Inactivation of Soluble Subtilisin in Organic Solvents. The rapid loss of activity in THF is depicted in FIG. 5. When assayed in THF, subtilisin loses 99% of its activity in less than 10 min. Much of this inactivated enzyme can be regenerated, however, upon transfer of the soluble enzyme to either water or octane. For example, transfer of subtilisin to water (by taking an aliquot of enzyme from the THF solution and diluting into aqueous buffer) after 10 min resulted in the regain of over one-third of the native enzyme activity (FIG. 5). Thus, soluble subtilisin inactivates quickly in dry THF, but can be partially renatured by transferring the enzyme to water. Similarly, transferring the enzyme from THF to octane also results in a regain of a portion of the active subtilisin, albeit a lesser fraction than that observed in water (FIG. 5, diamonds). After the rapid, partial reactivation, the fraction of active enzyme in octane does not measurably change further for up to 30 min. Subsequent transfer of the partially reactivated enzyme in octane to water, however, results in a fraction of active enzyme similar to that observed for the direct transfer of enzyme from THF to water Thermal inactivation of soluble subtilisin BPN[1] in octane. Similar inactivation and reactivation behavior was observed using elevated temperature as the denaturant in octane. Subtilisin was incubated in octane at 70° C. for various lengths of time and the activity of the enzyme was assayed in octane at 70° C., in octane at 25° C., and following extraction into water at 25° C. Three distinct trends were observed. First, in contrast to the high stability of soluble subtilisin at 25° C., over 98% of enzymatic activity is lost after 30 minutes of incubation at 70° C. in octane. Second, the majority of the inactivated enzyme can be renatured by extraction back into aqueous buffer at 25° C. Third, a significant fraction of the enzyme can also be renatured in octane by rapid cooling of the enzyme solution to 25° C., albeit a smaller fraction than in water.

Thus, enzyme-surfactant ion pairs according to the invention can refold to native conformation in organic solvents. This approach can only be applied using organic solvent-soluble enzymes according to the invention. Preferably, the temperature and polarity of the reaction solution are selected by approaches within the level of ordinary skill to maintain adequate activity and stability, as described above.

The high catalytic activity of subtilisin BPN' in nonpolar organic solutions contrasts greatly with the activity of the suspended enzyme, and this appears to be due to the maintenance of the secondary and tertiary structure of the soluble enzyme when extracted out of an aqueous solution into a nonpolar organic solvent. A major difference between the two preparations is that the suspended enzyme form undergoes lyophilization whereas the soluble enzyme form undergoes a liquid—liquid extraction followed by gaseous drying. Lyophilization can induce conformational changes in a protein which can only reverse to the native structure in aqueous solutions. The suspended enzyme, therefore, may be much less active than its soluble counterpart because it exists in the partially denatured form in organic solvents. The soluble enzyme is also more conformationally flexible than its insoluble counterpart. Such increased flexibility, particularly at the active site of the enzyme, can promote enzyme activity in organic solvents.

Subsequent drying of the extracted protein without freezing does not destroy the native structure of the enzyme. Soluble subtilisin is very stable in octane, and, presumably because of the absence of autolysis in octane and decreased flexibility, the enzyme is substantially more stable than in aqueous solutions. Assuming substrate saturating conditions, a practical measure of the operational value of an enzyme is its number of turnovers accomplished in a single half-life of the enzyme. This dimensionless term (represented by $k_{cat} \times \tau_{1/2}$) provides a general measure for the operational power of a biocatalyst. For the soluble enzyme in octane, this value is $1.0 \times 10^7$ (based on a half life of 2 months) and is greater than the value in water ($1.2 \times 10^6$). Thus, soluble subtilisin BPN' is a practical biocatalyst in octane.

EXAMPLE 8

Acryloyl chloride was added to a pH 8 solution of 1.5 mg/ml CT, at a molar ratio of 100:1, and was desalted. 2 mM $CaCl_2$ was added with 1% (v/v) of 1-propanol. The solution was mixed with an equal volume of isooctane containing 0.2 M AOT. The organic phase was removed following phase separation and was dried. The enzyme concentration was adjusted to about 1 to 10 mg/ml with an organic solvent. To 2 ml of this solution, 0.5 ml of a vinyl monomer was added, chosen from methyl methacrylate, vinyl acetate, ethyl vinyl ether, and styrene. A crosslinker (trimethylolpropane trimethylacrylate or divinylbenzene) was added to about 20% (v/v). An initiator, 2,2'-azobis-(2,4-dimethylvaleronitrile) was added and polymerization was produced by UV light. The resulting polymer was washed in hexane and then water.

FIG. 7 demonstrates that the catalyst composites are effective for peptide synthesis.

FIG. 8 shows the activity of CT-polymers in tert-amyl alcohol with small amounts of water. The initial reaction rates were measured for a transesterification reaction:

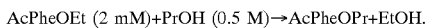

AcPheOEt (2 mM)+PrOH (0.5 M)→AcPheOPr+EtOH.

The water contents were 0.5%, 1.0%, and 1.5%. Lyophilized CT was used as control. The test samples contained polyvinylacetate, polymethylmethacrylate, polystyrene, and polyethylvinylethylene.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. Other enzymes, surfactants, solvents, and substrates may be used in similar manner or using minor variations according to techniques known in the art. It is therefore to be understood that, within the scope of the claims and their equivalents, the invention may be practiced otherwise than as specifically described.

What is claimed is:

1. A method of catalysis of at least one substrate into a product in an organic reaction solvent, comprising the steps of:
   (a) obtaining a catalyst comprising an enzyme-surfactant ion pair complex comprising an enzyme and an ionic surfactant capable of forming an ion pair complex with the enzyme, the complex being produced by extracting an aqueous solution of the enzyme with the ionic surfactant and a water immiscible organic solvent,
   (b) combining the catalyst with an organic reaction solvent, comprising an organic solvent and water in an amount sufficient to increase the rate of catalysis relative to a water-free organic reaction solvent, the amount of water ranging from about 0.03% to about 2.5% v/v, and
   (c) allowing catalysis of the at least one substrate into the product.

2. The method of claim 1, further comprising recovering the product after catalysis is substantially completed.

3. The method of claim 2, further comprising precipitating the enzyme from the organic reaction solvent by removal of the surfactant from the enzyme-surfactant complex after catalysis.

4. The method of claim 1, further comprising continuously adding the at least one substrate to the organic reaction solvent during catalysis.

5. The method of claim 1, further comprising removing the product from the organic reaction solvent continuously during catalysis.

6. The method of claim 1, in which the at least one substrate comprises an acyl donor and a nucleophile, and the catalysis is peptide synthesis.

7. The method of claim 6 in which the acyl donor is a methyl or ethyl ester of tyrosine, tryptophan, alanine, or phenylalanine; a methyl or ethyl ester of a dipeptide or tripeptide containing any of tyrosine, tryptophan, alanine, or phenylalanine; or an N-benzoyl, N-acetyl, or N-carbobenzoxy derivative thereof; and the nucleophile is an amino acid amide.

8. The method of claim 6, in which the amount of water present does not cause a substantial increase in hydrolysis compared to dry solvent and wherein the water is greater than about 0.03%.

9. The method of claim 1, in which the at least one substrate comprises at least one of an amino acid, an amino acid ester, an N-blocked amino acid, an N-blocked amino acid ester, an amino acid amide, an N-blocked amino acid amide, a polypeptide, a polypeptide ester, an N-blocked polypeptide, an N-blocked polypeptide ester, a polypeptide amide, an N-blocked polypeptide-amide.

10. The method of claim 1, in which the amount of water present causes a measurable increase in yield.

11. The method of claim 1, in which the water content of the reaction solvent does not exceed the water saturation point for the organic solvent containing the surfactant.

12. The method of claim 1, in which the molar ratio of water to enzyme in the organic reaction solvent is less than about 75:1.

13. The method of claim 1, further comprising the step of adding up to about 2.5% v/v water to the reaction solvent.

14. The method of claim 1, in which the organic reaction solvent comprises a water miscible hydrophilic organic solvent.

15. The method of claim 1 in which the enzyme is selected from the group consisting of a catalytic antibody, an oxidoreductase, a transferase, a lyase, an isomerase, a ligase, a hydrolase with acyl transferase activity in organic solvents, a peroxidase catalyzing phenolic polymerizations, a tyrosinase catalyzing aromatic hydroxylations, an alcohol dehydrogenase catalyzing stereoselective oxidation and reduction, a lipase, a nuclease, an aldolase, a phosphatase, a sulfatase, subtilisin, papain, pepsin, thermolysin, and thrombin.

16. The method of claim 1, wherein the amount of water in the reaction solvent is between about 0.1% and about 0.3%.

17. The method of claim 1, wherein the half life of the enzyme activity of the catalyst is at least about 0.25 hours.

18. The method of claim 1, wherein the half life of the enzyme activity of the catalyst is at least about one hour.

19. The method of claim 1, wherein the number of turnovers catalyzed by the enzyme-surfactant ion pair complex in the organic reaction solvent during one half life is greater than that of the enzyme dissolved in water.

20. A catalytic preparation comprising:
(a) a catalyst comprising an enzyme-surfactant ion pair complex comprising an enzyme and an ionic surfactant capable of forming an ion pair complex with the enzyme, the complex being produced by extracting an aqueous solution of the enzyme with the ionic surfactant and a water immiscible organic solvent, and
(b) an organic reaction solvent, comprising an organic solvent and water in an amount sufficient to increase the rate of catalysis relative to a water-free organic solvent, the amount of water ranging from about 0.03% to about 2.5% v/v.

* * * * *